(12) United States Patent
Liu et al.

(10) Patent No.: US 7,211,568 B2
(45) Date of Patent: May 1, 2007

(54) 9-DESOXOERYTHROMYCIN COMPOUNDS AS PROKINETIC AGENTS

(75) Inventors: Yaoquan Liu, Castro Valley, CA (US); Christopher Carreras, Belmont, CA (US); David C. Myles, Kensington, CA (US)

(73) Assignee: Kosan Biosciences Incorporated, Hayward, CA (US)

( * ) Notice: Subject to any disclaimer, the term of this patent is extended or adjusted under 35 U.S.C. 154(b) by 194 days.

(21) Appl. No.: 11/016,529

(22) Filed: Dec. 15, 2004

(65) Prior Publication Data

US 2005/0256064 A1    Nov. 17, 2005

Related U.S. Application Data

(60) Provisional application No. 60/531,163, filed on Dec. 18, 2003.

(51) Int. Cl.
 A61K 31/70    (2006.01)
 C07H 17/08   (2006.01)

(52) U.S. Cl. .......................................... 514/29; 536/7.2

(58) Field of Classification Search ................. 536/7.2; 514/29
See application file for complete search history.

(56) References Cited

U.S. PATENT DOCUMENTS

| | | | |
|---|---|---|---|
| 4,382,085 A | 5/1983 | Sciavolino et al. | |
| 4,382,086 A | 5/1983 | Sciavolino et al. | |
| 4,857,641 A | 8/1989 | Hauske | |
| 5,008,249 A | 4/1991 | Omura et al. | |
| 5,175,150 A | 12/1992 | Omura et al. | |
| 5,470,961 A | 11/1995 | Harada et al. | |
| 5,523,401 A | 6/1996 | Freiberg et al. | |
| 5,523,418 A | 6/1996 | Freiberg et al. | |
| 5,538,961 A | 7/1996 | Freiberg et al. | |
| 5,554,605 A | 9/1996 | Freiberg et al. | |
| 5,578,579 A | 11/1996 | Lartey et al. | |
| 5,654,411 A | 8/1997 | Lartey et al. | |
| 5,658,888 A | 8/1997 | Koga et al. | |
| 5,712,253 A | 1/1998 | Lartey et al. | |
| 5,834,438 A | 11/1998 | Lartey et al. | |
| 5,922,849 A | 7/1999 | Premchandran et al. | |
| 5,959,088 A | 9/1999 | Miura et al. | |
| 6,084,079 A | 7/2000 | Keyes et al. | |
| 6,169,168 B1 | 1/2001 | Asaka et al. | |
| 6,492,562 B1 | 12/2002 | Ashley et al. | |
| 6,514,944 B2 | 2/2003 | Chu et al. | |
| 6,667,338 B2 | 12/2003 | Ma et al. | |
| 6,762,168 B2 | 7/2004 | Chu et al. | |
| 6,946,482 B2* | 9/2005 | Santi et al. | 514/450 |
| 2002/0025936 A1 | 2/2002 | Ashley et al. | |
| 2002/0094962 A1 | 7/2002 | Ashley et al. | |
| 2002/0132782 A1 | 9/2002 | Ma et al. | |
| 2002/0156028 A1 | 10/2002 | Chu et al. | |
| 2002/0192709 A1 | 12/2002 | Carreras et al. | |
| 2004/0138150 A1 | 7/2004 | Santi et al. | |

FOREIGN PATENT DOCUMENTS

JP    60-218321    11/1985

OTHER PUBLICATIONS

U.S. Appl. No. 10/926,170, filed Aug. 24, 2004, Carreras et al.
Carreras et al., *Anal. Biochemistry*, 300, 146-151 (2002), "Stable Expression of a Synthetic Gene for Human Motilin Receptor: Use in an Aequorin-Based Receptor Activation Assay".
Chemical Abstracts No. 104:82047 (abstract of JP 60-218321).
Depoortere et al., *J. Gastrointestinal Motility*, 1, 150-159 (1989), "Structure-Activity Relation of Erthromycin-Related Macrolides in Inducing Contractions and in Displacing Bound Motilin in Rabbit Duodenum".
Desai et al., *Biotechnol. Prog.* 20, 1660-1665 (2000), "Improved Bioconversion of 15-Fluoro-6-deoxyerythro-nolide B to 15-Fluoroerythromycin A by Overexpression of the eryK Gene in *Saccharopolyspora erythraea*".

(Continued)

*Primary Examiner*—Elli Peselev
(74) *Attorney, Agent, or Firm*—Yuan Chao

(57) ABSTRACT

9-Desoxoerythromycin compounds of formula I

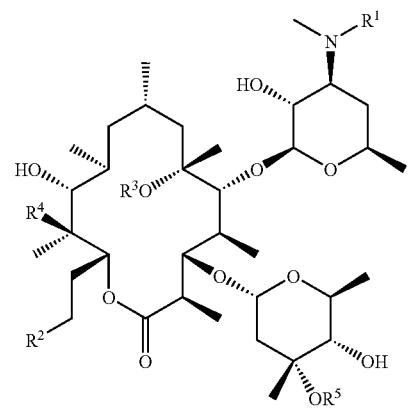

wherein $R^1$, $R^2$, $R^3$, $R^4$, and $R^5$ are as defined herein, are useful as prokinetic agents for treating disorders of gastric motility.

15 Claims, 2 Drawing Sheets

OTHER PUBLICATIONS

Faghih et al., *Biorg. & Med. Chem. Lett.*, 8 (1998), 805-810, "Preparation of 9-Deoxo-4"-deoxy-6,9-epoxyerythromycin Lactams 'Motilactides': Potent and Orally Active Prokinetic Agents".

Faghih et al., *Drugs of the Future*, 23 (8), 861-872 (1998), "Motilides and motilactides: design and development of motilin receptor agonists as a new class of gastrointestinal prokinetic drugs".

Faghih et al., *J. Antibiotics*, 43 (10), 1334-1336 (1990), "Synthesis and Antibacterial Activity of (9S)-9-Dihydroclarithromycin".

Faghih et al., *J. Med. Chem.*, 1998, 41, 3402-3408, "Synthesis of 9-Deoxo-4"-deoxy-6,9-epoxyerythromycin Derivatives: Novel and Acid-Stable Motilides".

Faghih et al., *Synlett* 751 (Jul. 1998), "Entry into Erythromycin Lactams: Synthesis of Erythromycin A Lactam Enol Ether as a Potential Gastrointestinal Prokinetic Agent".

Hauske et al., *J. Org. Chem.* 49, 712-714 (1984), "Regiospecific Synthesis of 9-Desoxo Erythromycin A".

Ku et al., *J. Antibiotics* 52 (10), 908-912 (1999), "Synthesis and Antibacterial Activities of Novel 12-O-Methylerythromycin A Derivatives".

Ku et al., *J. Org. Chem.* 64, 2107-2109 (1999), Synthe-sis of a Novel Macrolide: 9(S)-9-Dihydro-12-O-Methyl-erythromycin A via Regioselective Methylation.

Lartey et al., *J. Med. Chem.*, 38, 1793-1798 (1995), "Synthesis of 4"-Deoxy Motlildes: Identification of a Potent and Orally Active Prokinetic Drug Candidate".

Omura et al., *J. Antibiotics* (1985), 38, 1631-2, "Gastroin-testinal Motor-Stimulating Activity of Macrolide Antibiotics and the Structure-Activity Relationship".

Stanat et al., *Mol. Cellular Biochem.*, 254, 1-7 (2003), "Characterization of the Inhibitory Effects of Erythromycin and Clarithromycin on the HERG Potassium Channel".

Stresser et al., *Drug Metabolism Disposition*, 30 (7), 845-52 (2002), "Cytochrome P450 Fluorometric Substrates: Identification of Isoform-Selective Probes for Rat CYP2D2 and Human CYP3A4".

Wermuth, "Designing Prodrugs and Bioprecursors," in Wermuth, ed., *The Practice of Medicinal Chemistry*, 2nd Ed., pp. 561-586 (Academic Press 2003).

\* cited by examiner

9-DESOXOERYTHROMYCIN COMPOUNDS AS PROKINETIC AGENTS

CROSS-REFERENCE TO RELATED APPLICATIONS

This application claims the benefit under 35 USC §119(e) of U.S. Provisional Application No. 60/531,163, filed Dec. 18, 2003, the disclosure of which is incorporated herein by reference.

BACKGROUND OF THE INVENTION

1. Field of the Invention

This invention relates to 9-desoxoerythromycin compounds, methods of making them, and their use as prokinetic agents.

2. Description of Related Art

Gastrointestinal ("GI") motility regulates the orderly movement of ingested material through the gut to ensure adequate absorption of nutrients, electrolytes, and fluids. Proper transit of the GI contents through the esophagus, stomach, small intestine, and colon depends on regional control of intraluminal pressure and several sphincters, which regulate their forward movement and prevent backflow. The normal GI motility pattern may be impaired by a variety of circumstances, including disease and surgery.

GI motility disorders include gastroparesis and gastroesophageal reflux disease ("GERD"). Gastroparesis, whose symptoms include stomach upset, heartburn, nausea, and vomiting, is the delayed emptying of stomach contents. GERD refers to the varied clinical manifestations of the reflux of stomach and duodenal contents into the esophagus. The most common symptoms are heartburn and dysphasia, with blood loss from esophageal erosion also known to occur. Other examples of GI disorders in which impaired GI motility is implicated include anorexia, gall bladder stasis, postoperative paralytic ileus, scleroderma, intestinal pseudoobstruction, irritable bowel syndrome, gastritis, emesis, and chronic constipation (colonic inertia).

Motilin is a 22-amino acid peptide hormone secreted by endocrine cells in the intestinal mucosa. Its binding to the motilin receptor in the GI tract stimulates GI motility. The administration of therapeutic agents that act as motilin receptor agonists ("prokinetic agents") has been proposed as a treatment for GI disorders.

The erythromycins are a family of macrolide antibiotics made by the fermentation of the Actinomycetes *Saccharopolyspora erythraea*. Erythromycin A, a commonly used antibiotic, is the most abundant and important member of the family.

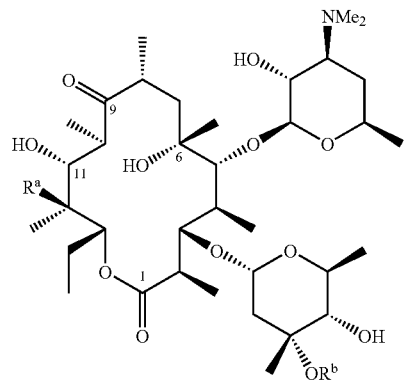

| | | |
|---|---|---|
| (1) Erythromycin A | $R^a$ = OH | $R^b$ = Me |
| (2) Erythromycin B | $R^a$ = H | $R^b$ = Me |
| (3) Erythromycin C | $R^a$ = OH | $R^b$ = H |
| (4) Erythromycin D | $R^a$ = H | $R^b$ = H |

The side effects of erythromycin A include nausea, vomiting, and abdominal discomfort. These effects have been traced to motilin receptor agonist activity in erythromycin A (1) and, more so, its initial acid-catalyzed degradation product (5). (The secondary degradation product, spiroketal (6), is inactive.)

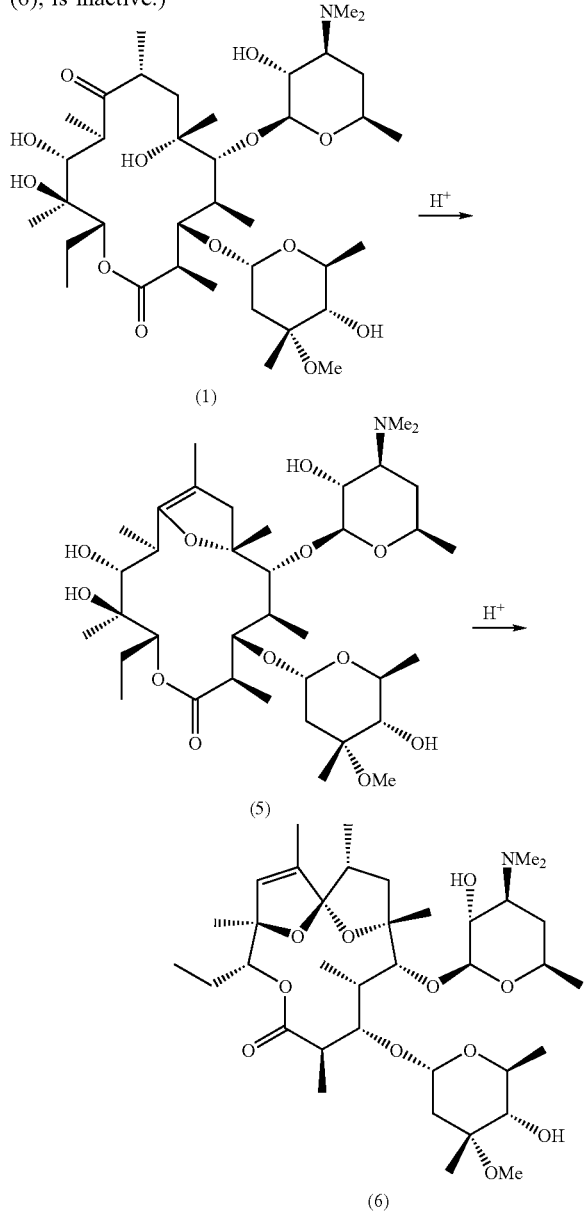

Spurred by the discovery of motilin agonist activities in erythromycin A and degradation product (5), researchers have endeavored to discover new motilides, as macrolides with prokinetic activity are called. Much of the research has centered on generating new erythromycin analogs, either via post-fermentation chemical transformation of a naturally produced erythromycin or via modification (including genetic engineering) of the fermentation process. Illustrative disclosures relating to motilides based on an erythromycin scaffold include: Omura et al., U.S. Pat. No. 5,008,249 (1991) and U.S. Pat. No. 5,175,150 (1992); Harada et al., U.S. Pat. No. 5,470,961 (1995); Freiberg et al., U.S. Pat. No. 5,523,401 (1996); U.S. Pat. No. 5,523,418 (1996); U.S. Pat. No. 5,538,961 (1996); and U.S. Pat. No. 5,554,605 (1996); Lartey et al., U.S. Pat. No. 5,578,579 (1996); U.S. Pat. No. 5,654,411 (1997); U.S. Pat. No. 5,712,253 (1998); and U.S. Pat. No. 5,834,438 (1998); Koga et al., U.S. Pat. No. 5,658,888 (1997); Miura et al., U.S. Pat. No. 5,959,088 (1998); Premchandran et al., U.S. Pat. No. 5,922,849 (1999); Keyes et al., U.S. Pat. No. 6,084,079 (2000); Ashley et al., US 2002/0025936 A1 (2002); Ashley et al., US 2002/0094962 A1 (2002); Carreras et al., US 2002/0192709 A1 (2002); Ito et al., JP 60-218321 (1985) (corresponding Chemical Abstracts abstract no. 104:82047); Santi et al., U.S. patent application Ser. No. 10/648,946, filed Aug. 26, 2003; Carreras et al., US Provisional Patent Application No. 10/920,170, filed Aug. 24, 2004; Omura et al., "Gastrointestinal Motor-Stimulating Activity of Macrolide Antibiotics and the Structure-Activity Relationship," *J. Antibiotics* (1985), 38, 1631–2; Faghih et al., "Preparation of 9-Deoxo-4"-deoxy-6,9-epoxyerythromycin Lactams 'Motilactides': Potent and Orally Active Prokinetic Agents," *Biorg. & Med. Chem. Lett.,* 8 (1998), 805–810; Faghih et al., "Synthesis of 9-Deoxo-4"-deoxy-6,9-epoxyerythromycin Derivatives: Novel and Acid-Stable Motilides," *J. Med. Chem.,* 1998, 41, 3402–3408; Faghih et al., "Entry into Erythromycin Lactams: Synthesis of Erythromycin A Lactam Enol Ether as a Potential Gastrointestinal Prokinetic Agent," *Synlett* 751 (July 1998); and Lartey et al., *J. Med. Chem.,* 38, 1793–1798 (1995), "Synthesis of 4"-Deoxy Motilides: Identification of a Potent and Orally Active Prokinetic Drug Candidate"; the disclosures of which are incorporated herein by reference.

A number of parameters are relevant to the development of erythromycin analogs as motilides. Firstly, the evolution of the erythromycin scaffold in the natural producing organisms has been driven by antibacterial efficacy and not by prokinetic efficacy. Therefore, considerable room remains for optimization of the structure-activity relationship for motilin receptor agonist activity. Secondly, it is in fact undesirable for a motilide to possess antibacterial activity. The GI tract is host to a large population of bacteria, whose exposure to a motilide having antibacterial activity may induce the development in them of resistance to erythromycin antibiotics. Thus, a motilide desirably has enhanced prokinetic activity engineered in and antibacterial activity engineered out. Thirdly, a drawback commonly found among motilides evaluated to date is their propensity to desensitize the motilide receptor, meaning that, after the initial dose, subsequent doses of a motilide elicit a weaker or no response (tachyphylaxis). Fourthly, stability and bioavailability are concerns—witness the ready degradation of erythromycin A in the stomach and the lack of activity in its secondary degradation product. Fifthly, some compounds in the erythromycin family have been reported to have undesirable pro-arrhythmic effects, including the prolongation of the QT interval and the induction of ventricular arrhythmias. Limiting these effects to an acceptable level is desirable. Thus, there exists a continuing need to develop new motilides, balancing the various different performance requirements.

BRIEF SUMMARY OF THE INVENTION

In one aspect of the invention, there is provided a compound having a structure according to formula I:

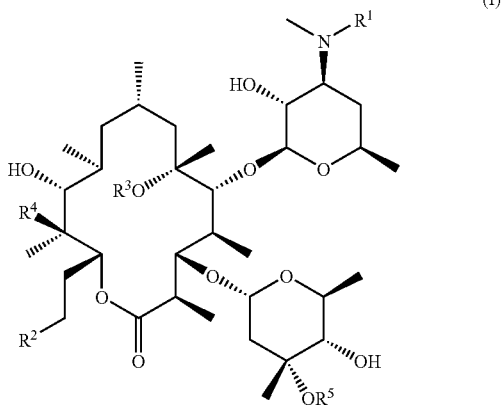

(I)

and the pharmaceutically acceptable salts, solvates, hydrates, and esters thereof, wherein
$R^1$ is $C_2$–$C_5$ alkyl, $C_2$–$C_5$ alkenyl, or $C_2$–$C_5$ alkynyl;
$R^2$ is H, Me, or F;
$R^3$ is H or Me;
$R^4$ is H or OH; and
$R^5$ is H or Me.

In a second aspect of the invention, the invention provides a method for treating a disorder of gastric motility in a subject suffering from such disorder, comprising administering to a subject in need of such treatment a therapeutically effective dose of compound I. The disorder of gastric motility can be gastroparesis, gastroesophageal reflux disease, anorexia, gall bladder stasis, postoperative paralytic ileus, scleroderma, intestinal pseudo-obstruction, gastritis, emesis, or chronic constipation (colonic inertia).

In a third aspect of the invention, compound I is used for the preparation of a medicament for treating a gastric motility disorder.

In a fourth aspect of the invention, there is provided a method for stimulating the motilin receptor, comprising contacting the motilin receptor with a compound having a structure according to formula I. The motilin receptor may be located inside a cell, or outside a cell.

DETAILED DESCRIPTION OF THE INVENTION

Definitions

Figure 1:
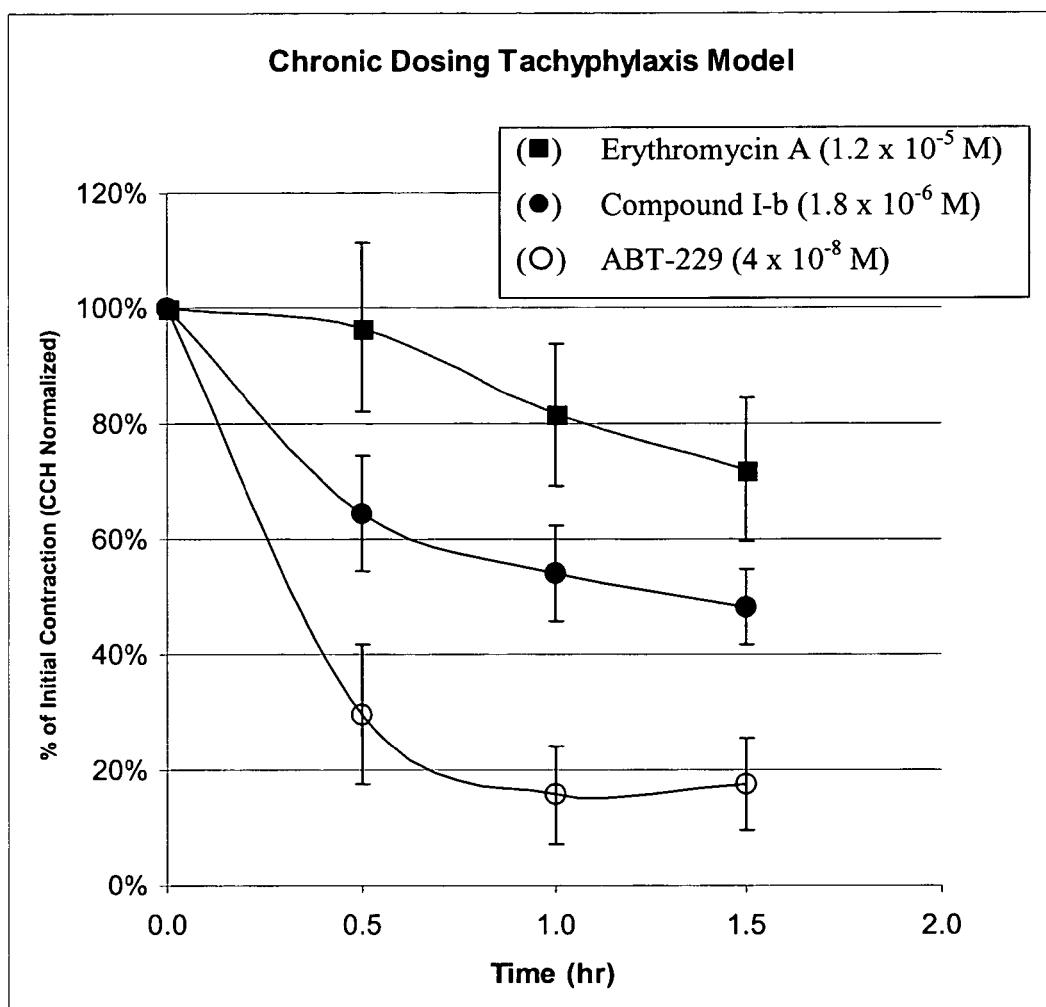
FIG. 1 shows the results for a chronic dosing tachphylaxis model for a compound of this invention.

The definitions of the terms given below apply to the terms as they are used throughout this specification and the appended claims, unless the context clearly indicates otherwise.

"Alkyl" means an optionally substituted straight or branched chain hydrocarbon moiety having the specified number of carbon atoms in the chain (e.g., as in "$C_2$–$C_5$ alkyl") or, where the number of carbon atoms is not specified, up to 3 carbon atoms in the chain.

"Alkenyl" means an optionally substituted straight or branched chain hydrocarbon moiety having at least one carbon-carbon double bond and the specified number of carbon atoms in the chain (e.g., as in "$C_2$–$C_5$ alkenyl") or, where the number of carbon atoms is not specified, up to 3 carbon atoms in the chain.

"Alkynyl" means an optionally substituted straight or branched chain hydrocarbon moiety having at least one carbon-carbon triple bond and the specified number of carbon atoms in the chain (e.g., as in "$C_2$–$C_5$ alkynyl") or, where the number of carbon atoms is not specified, up to 3 carbon atoms in the chain.

"Alkylaryl," "arylalkyl," "heterocycloalkyl," "alkylheteroaryl," "alkylheterocycle" and the like mean an aryl, heterocyclic, or heteroaryl group, as the case may be, bonded directly to an alkyl moiety, as in benzyl, phenethyl, and the like.

"Aryl" means a monocyclic or bicyclic aromatic hydrocarbon ring system having 6 to 12 carbon atoms in the ring portion, such as phenyl, napthyl, and biphenyl moieties, each of which is optionally substituted at one or more positions.

"Cycloalkyl" means an optionally substituted, saturated cyclic hydrocarbon ring system, preferably containing 1 to 3 rings and 3 to 7 carbons per ring (unless a different number of carbons is indicated), which may be further fused with an unsaturated $C_3$–$C_7$ carbocyclic ring. Exemplary cycloalkyl ring systems include cyclopropyl, cyclobutyl, cyclopentyl, cyclohexyl, cycloheptyl, cyclooctyl, cyclodecyl, cyclododecyl, and adamantyl.

"Halogen" or "halo" means fluorine, chlorine, bromine or iodine.

"Heterocycle", "heterocyclic," or "heterocyclo" means an optionally substituted, fully saturated or unsaturated, aromatic or nonaromatic ring system, for example, which is a 4 to 7 membered monocyclic, 7 to 11 membered bicyclic, or 10 to 15 membered tricyclic ring system, which has at least one heteroatom in at least one carbon atom-containing ring. "Heteroaryl" means a heterocycle in which the ring system is aryl. Each ring of the heterocyclic group containing a heteroatom may have 1, 2 or 3 heteroatoms selected from N, O and S, where the N and S optionally may be oxidized and the N optionally may be quaternized.

Exemplary monocyclic heterocyclic ring systems include pyrrolidinyl, pyrrolyl, indolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxazepinyl, azepinyl, 4-piperidonyl, pyridinyl, N-oxo-pyridyl, pyrazinyl, pyrimidinyl, pyridazinyl, tetrahydropyranyl, tetrahydrothiopyranyl, tetrahydrothiopyranyl sulfone, morpholinyl, thiomorpholinyl, thiomorpholinyl sulfoxide, thiomorpholinyl sulfone, 1,3-dioxolane and tetrahydro-1,1-dioxothienyl, dioxanyl, isothiazolidinyl, thietanyl, thiiranyl, triazinyl, and triazolyl, and the like. Preferred heterocyclo groups include pyridinyl, pyrazinyl, pyrimidinyl, pyrroyl, pyrazolyl, imidazolyl, thiazolyl, oxazolyl, isoxazolyl, thiadiazolyl, oxadiazolyl, thienyl, furanyl, quinolinyl, isoquinolinyl, and the like.

Where it is indicated that a group may be substituted, for example by use of "substituted or unsubstituted" or "optionally substituted" phrasing, such group may have one or more independently selected substituents, preferably one or two in number. It is understood that substituents and substitution patterns can be selected by one of ordinary skill in the art to provide compounds that are chemically stable and that can be synthesized by techniques known in the art as well as the methods set forth herein. Examples of suitable substituents include alkyl, alkenyl, alkynyl, aryl, halo, trifluoromethoxy, trifluoromethyl, hydroxy, alkoxy, cycloalkyloxy, heterocyclooxy, alkanoyl, alkanoyloxy, amino, alkylamino quarternary ammonium, aralkylamino, cycloalkylamino, heterocycloamino, dialkylamino, alkanoylamino, thio, alkylthio, cycloalkylthio, heterocyclothio, ureido, nitro, cyano, carboxy, carboxylalkyl, carbamyl, alkoxycarbonyl, alkylthiono, arylthiono, alkylsulfonyl, sulfonamido, aryloxy, and the like, in addition to those specified herein. The substituent may be further substituted, for example, by halo, hydroxy, alkyl, alkoxy; aryl, substituted aryl, substituted alkyl, substituted aralkyl, and the like. Preferably, the substituent(s) for alkyl, alkenyl, and alkynyl moieties are from one to three in number and are independently selected from N-pyrrolidinyl, N-morpholinyl, N-azetidinyl, hydroxyl, halo, alkoxyl, cyano, amino, alkylamino, and dialkylamino, especially when located at the β- or 2-position.

"Pharmaceutically acceptable ester" means an ester that hydrolyzes in vivo (for instance in the human body) to produce the parent compound or a salt thereof or has per se activity similar to that of the parent compound. Suitable ester groups include, without limitation, those derived from pharmaceutically acceptable aliphatic carboxylic acids, particularly alkanoic, alkenoic, cycloalkanoic and alkanedioic acids, in which each alkyl or alkenyl moiety preferably has no more than six carbon atoms. Illustrative esters include formates, acetates, propionates, butyrates, acrylates, citrates, succinates, and ethylsuccinates.

"Pharmaceutically acceptable salt" means a salt of a compound suitable for pharmaceutical formulation. Suitable pharmaceutically acceptable salts include acid addition salts which may, for example, be formed by mixing a solution of a compound with a solution of a pharmaceutically acceptable acid such as hydrochloric acid, hydrobromic acid, sulfuric acid, fumaric acid, maleic acid, succinic acid, benzoic acid, acetic acid, citric acid, tartaric acid, phosphoric acid, carbonic acid, or the like. Where a compound carries one or more acidic moieties, pharmaceutically acceptable salts may be formed by treatment of a solution of the compound with a solution of a pharmaceutically acceptable base, such as lithium hydroxide, sodium hydroxide, potassium hydroxide, tetraalkylammonium hydroxide, lithium carbonate, sodium carbonate, potassium carbonate, ammonia, alkylamines, or the like.

Unless particular stereoisomers are specifically indicated (e.g., by a bolded or dashed bond at a relevant stereocenter in a structural formula, by depiction of a double bond as having E or Z configuration in a structural formula, or by use stereochemistry-designating nomenclature), all stereoisomers are included within the scope of the invention, as pure compounds as well as mixtures thereof. Unless otherwise indicated, individual enantiomers, diastereomers, geometrical isomers, and combinations and mixtures thereof are all encompassed by the present invention. Polymorphic crystalline forms and solvates are also encompassed within the scope of this invention.

The present invention includes within its scope prodrugs of the compounds of this invention. Such prodrugs are in general functional derivatives of the compounds that are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to a subject in need thereof. Conventional procedures for the selection and preparation of suitable prodrug derivatives are described, for example, in Wermuth, "Designing Prodrugs and Bioprecursors," in Wermuth, ed., *The Practice of Medicinal Chemis-*

*try*, 2nd Ed., pp. 561–586 (Academic Press 2003), the disclosure of which is incorporated herein by reference. Prodrugs include esters that hydrolyze in vivo (for example in the human body) to produce a compound of this invention or a salt thereof. Suitable ester groups include, without limitation, those derived from pharmaceutically acceptable aliphatic carboxylic acids, particularly alkanoic, alkenoic, cycloalkanoic and alkanedioic acids, in which each alkyl or alkenyl moiety preferably has no more than six carbon atoms. Illustrative esters include but are not limited to formates, acetates, propionates, butyrates, acrylates, citrates, succinates, and ethylsuccinates.

Compounds and Methods

Erythromycin A derivatives having a basic atom at position C9 (9-keto, 9-oxime, 9-hydrazone, 9-amino, and the like) are usually highly active against Gram-positive bacteria. The reduction of the 9-keto group in erythromycin A (and its 6-OMe counterpart clarithromycin) has been reported to lead to a lesser but still significant residual antibacterial potency (Faghih et al., *J. Antibiotics*, 43 (10), 1334–1336 (1990), "Synthesis and Antibacterial Activity of (9S)-9-Dihydroclarithromycin"). Thus, although 9-dihydroerythromycin has good motilin agonist activity (Depoortere et al., *J. Gastrointestinal Motility*, 1, 150–159 (1989), "Structure-Activity Relation of Erythromycin-Related Macrolides in Inducing Contractions and in Displacing Bound Motilin in Rabbit Duodenum"), its residual antibacterial activity militates against its development as a therapeutically useful prokinetic agent.

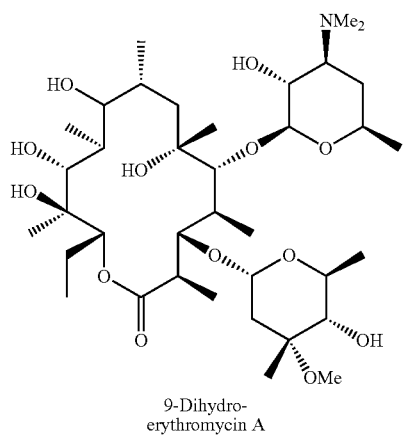

9-Dihydro-
erythromycin A

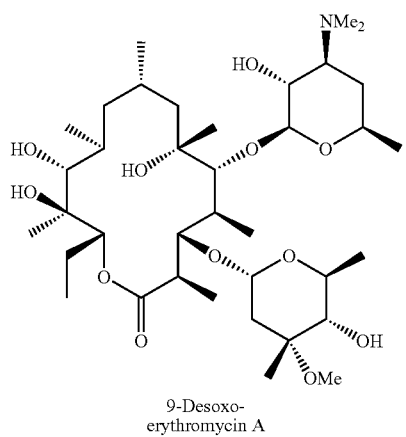

9-Desoxo-
erythromycin A

We have discovered a new class of prokinetic agents based on an erythromycin scaffold. By fully reducing the 9-keto group to a methylene group (9-desoxoerythromycin compounds) and replacing one of the N-methyl groups in the desosamine group, we have succeeded in decoupling prokinetic and antibacterial activity. Such decoupling enabled us to discover compounds having efficacious motilin agonist activity and substantially no antibacterial activity. (Although 9-desoxoerythromycin A itself has been prepared (see Hauske et al., *J. Org. Chem.* 49, 712–714 (1983)), it has not been investigated or proposed as a prokinetic agent.)

In a preferred embodiment, $R^3$ is H, $R^4$ is OH, and $R^5$ is Me, corresponding to a compound having a structure according to formula Ia:

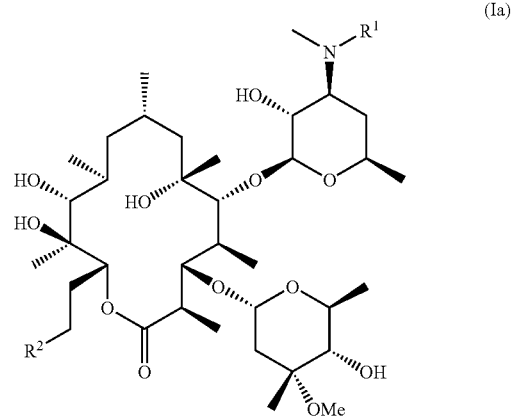

(Ia)

Referring to formulae I and Ia, $R^1$ preferably is isopropyl, sec-butyl, n-propyl, 2-hydroxyethyl, 2-hydroxy-2-methylpropyl, t-butyl, 2-ethoxyethyl, or isobutyl; more preferably isopropyl, sec-butyl, isobutyl, or 2-hydroxyethyl. $R^2$ preferably is H. Without being bound by theory, it is believed that the desosamine $NMe_2$ group in erythromycin binds to bacterial ribosomes, accounting for its antibacterial activity. Replacing the $NMe_2$ group with a larger $NMeR^1$ group has the effect of interfering with such binding and reducing antibacterial activity.

Specific compounds of this invention include:

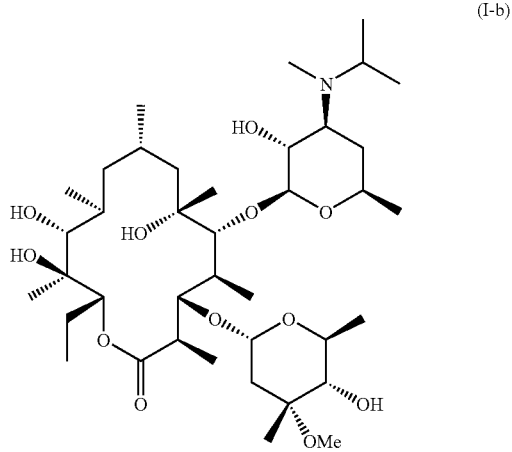

(I-b)

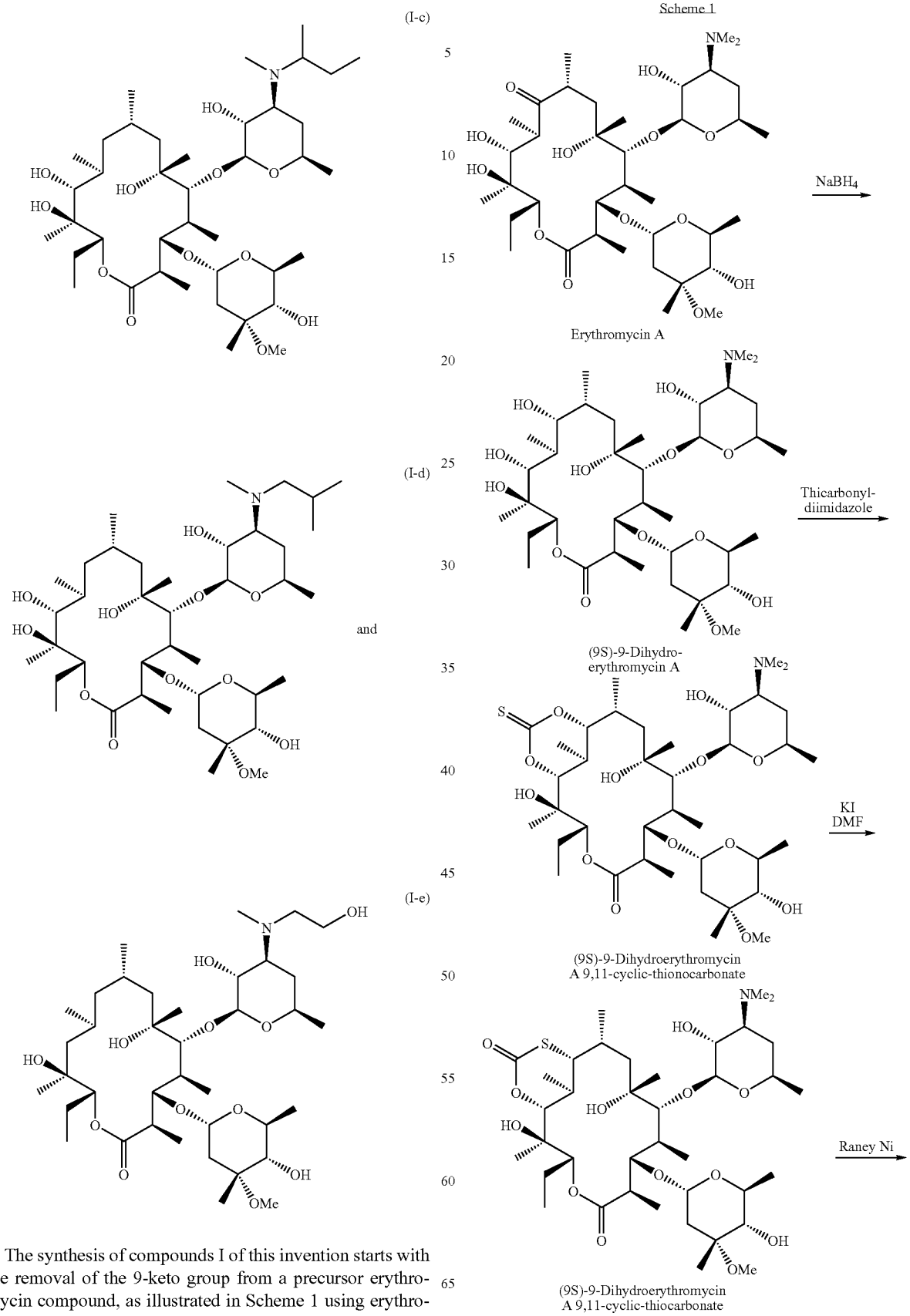
The synthesis of compounds I of this invention starts with the removal of the 9-keto group from a precursor erythromycin compound, as illustrated in Scheme 1 using erythromycin A as an archetype:

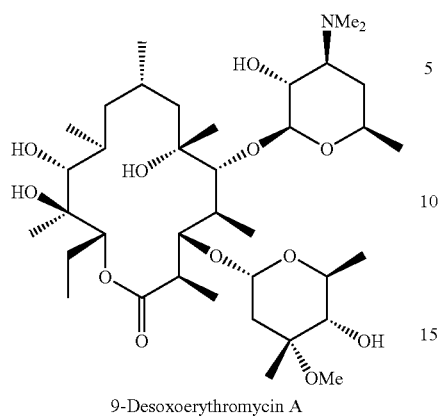

9-Desoxoerythromycin A

The 9-desoxo compounds obtained by the procedure of Scheme 1 are then converted to compounds of this invention by the procedure of Scheme 2:

Scheme 2

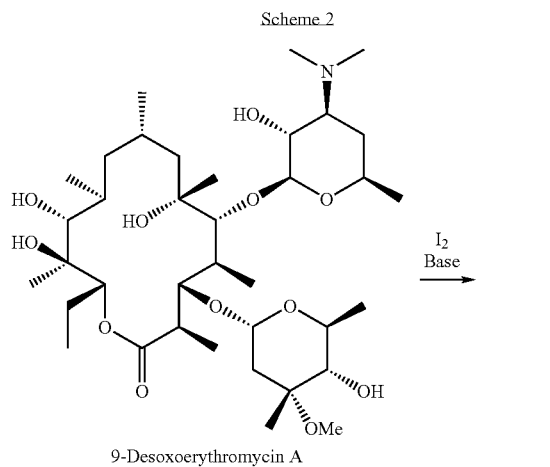

9-Desoxoerythromycin A $\xrightarrow{\text{I}_2 \text{ Base}}$

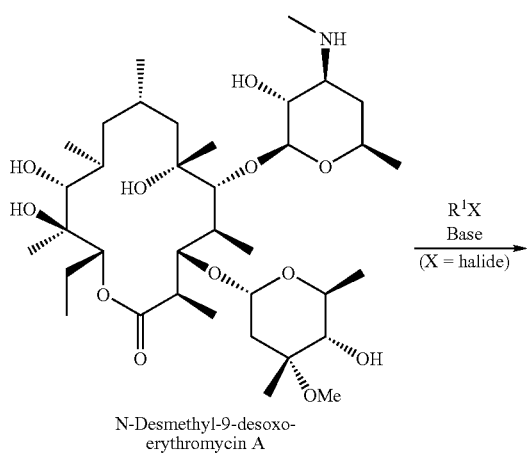

N-Desmethyl-9-desoxo-erythromycin A $\xrightarrow[\text{(X = halide)}]{\text{R}^1\text{X Base}}$

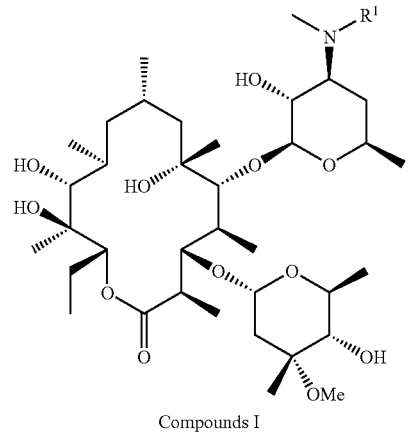

Compounds I

The practice of this invention can be further understood by reference to the following examples, which are provided by way of illustration and not of limitation.

EXAMPLE 1

9-Desoxoerythromycin A

9-Desoxoerythromycin A was prepared as shown in Scheme 1, following the procedure of Hauske et al., *J. Org. Chem.*, 49, 712–714 (1984).

(9S)-9-Dihydroerythromycin A. To a solution of erythromycin A (22.0 g, 30 mmol) in THF (200 mL) cooled to –10° C. was added NaBH$_4$ (2.27 g, 60 mmol) in small portions. The mixture was then allowed to stir at 0° C. for 3 h before the reaction was quenched with water. After evaporation of the majority of the solvent, dilute NaHCO$_3$ solution was added, the mixture was extracted three times with EtOAc. The combined organic layers were washed with water and brine, dried over MgSO$_4$. The crude product was purified by silica gel chromatography using 2:1 hexane-acetone with 1% Et$_3$N to give pure product (12.8 g, 58% yield). m/z: 736.5 (MH); $^{13}$C-NMR (CDCl$_3$): 177.00, 103.21, 96.32, 84.20, 83.10, 79.23, 77.72, 77.63, 74.99, 74.48, 72.66, 70.75, 70.69, 69.29, 66.09, 65.02, 49.32, 45.52, 41.73, 40.32 (2×), 36.91, 34.84, 34.23, 31.97, 28.81, 25.25, 21.68, 21.51, 21.18, 20.06, 18.12, 16.50, 15.06, 14.80, 10.81, 9.36.

(9S)-9-Dihydroerythromycin A 9,11-cyclic-thionocarbonate. To a solution of (9S)-9-dihydroerythromycin A (3.70 g, 5.0 mmol) and anhydrous K$_2$CO$_3$ (1.74 g, 12.5 mmol) in acetone (15 mL) was added thiocarbonyldiimidazole (0.98 g, 5.5 mmol). The mixture was stirred at room temperature for 3 h. The reaction was judged complete when the starting material could no longer be seen by thin-layer chromatographic analysis. The mixture was then diluted with EtOAc, washed three times with water, and once with brine, dried over MgSO$_4$. After evaporation of solvent the crude product was purified by silica gel chromatography (2% to 5% methanol in CH$_2$Cl$_2$ with 1% Et$_3$N), 2.90 g (75% yield) desired product was obtained. m/z: 778.6 (MH); $^{13}$C-NMR (CDCl$_3$): 190.64, 175.56, 104.78, 97.74, 89.94, 87.53, 86.96, 79.62, 78.94, 77.52, 76.77, 74.09, 72.51, 70.49, 69.5, 66.16, 64.66, 49.35, 46.96, 41.86, 40.29 (2×), 37.52, 34.86, 34.15, 34.02, 28.87, 25.01, 22.93, 21.36, 21.09, 21.02, 17.83, 16.04, 15.48, 14.00, 10.67, 9.78.

9-Dihydroerythromycin A 9,11-cyclic-thiocarbonate. To a solution of (9S)-9-dihydroerythromycin A 9,11-cyclicthionocarbonate (2.80 g, 3.6 mmol) in N,N-dimethylformamide (20 mL) was added in one portion KI (5.60 g, 33.7 mmol). The resulting solution was stirred under nitrogen at 130° C. for 3 h. After cooling to room temperature the reaction mixture was diluted with EtOAc, washed three times with water, and once with brine, dried over MgSO$_4$. After evaporation of solvent the crude product (2.80 g) was obtained, which was used directly for next step without purification.

9-Desoxoerythromycin A. The above crude product was dissolved in EtOH (50 mL), under nitrogen atmosphere, followed by addition of Raney Ni (5.60 g). The resulting slurry was then heated under reflux for 2 h. After cooling to room temperature the mixture was filtered through Celite and the Celite was washed twice with EtOH. The filtrate and washes were concentrated in vacuo, and then purified with silica gel chromatography (30% to 60% acetone in hexane, with 1% Et$_3$N) to give pure product (2.0 g, 77% yield for last 2 steps). m/z: 720.4 (MH); $^{13}$C-NMR (CDCl$_3$): 178.46, 101.64, 95.06, 81.47, 78.41, 77.98, 77.76, 77.21, 75.09, 74.99, 72.73, 71.03, 69.36, 68.30, 66.63, 64.99, 49.25, 44.98, 44.74, 41.34, 40.40 (2×), 34.65, 29.25, 28.92, 26.87, 25.42, 22.64, 21.73, 21.30, 21.19, 18.08, 16.07, 15.23, 13.87, 11.21, 8.91.

EXAMPLE 2

Compounds I

The 9-desoxoerythromycin A made in the preceding example was used to produce compounds I via the procedure outlined in Scheme 2. The detailed procedure given below for N-desmethyl-N-isopropyl-9-desoxoerythromycin A (Compound I-b) is representative.

N-Desmethyl-9-desoxoerythromycin A. A mixture of 9-desoxoerythromycin A (400 mg, 0.55 mmol) and NaOAc (0.62 g, 7.56 mmol) in MeOH-water (8:2 V/V, 10 mL) was stirred at 50° C. Iodine (0.42 g, 1.65 mmol) was then added. During the reaction 2N NaOH (0.82 mL) was added in small portions. Complete reaction was determined by thin-layer chromatographic analysis. After removal of solvent the mixture was extracted three times with EtOAc and dried over Na$_2$SO$_4$. Crude product was purified by silica gel chromatography (1:1 hexane-acetone, 1% Et$_3$N) to give N-desmethyl 9-desoxoerythromycin A (210 mg, 54% yield). m/z: 706.3 (MH); $^{13}$C-NMR (CDCl$_3$): 178.00, 102.21, 95.59, 83.89, 78.77, 78.08, 77.43 (2×), 74.95, 74.93, 74.22, 72.73, 68.98, 68.58, 66.63, 59.87, 49.10, 45.14, 44.19, 42.31, 41.33, 36.75, 34.75, 32.99, 29.12, 26.67, 22.62, 21.53, 21.17, 20.87, 18.02, 16.06, 15.28, 14.54, 9.78, 9.26.

N-Desmethyl-N-isopropyl-9-desoxoerythromycin A (Compound I-b). A mixture of N-desmethyl 9-desoxoerythromycin A (176 mg, 0.25 mmol), diisopropylethylamine (0.44 mL, 10 equiv), 2-bromopropane (600 mg, 20 equiv) in acetonitrile (10 mL) was heated in a 70° C. bath for overnight. Water and saturated NaHCO$_3$ were added, the solution was extracted three times with EtOAc, and dried over MgSO$_4$. The crude product was purified with a silica gel column (3:1 hexane-acetone, 1% Et$_3$N) to give pure product (116 mg, 62% yield).). m/z: 748.5 (MH); $^{13}$C-NMR (CDCl$_3$): 178.55, 101.49, 95.02, 81.03, 78.43, 77.86 (2×), 75.09, 74.96, 72.69, 70.33, 69.28, 68.45, 66.47 (2×), 61.75, 52.62, 49.23, 45.01, 44.76, 43.44, 41.23, 34.64, 32.93, 31.18, 29.21, 26.86, 25.43, 22.62, 21.69, 21.23, 21.21, 20.36, 18.09, 16.06, 15.23, 13.86, 11.17, 8.82.

Compounds I-c, 1-d and I-e were similarly prepared, using sec-butyl iodide, isobutyl iodide, and 2-iodoethanol, respectively as the alkyl halides. Their analytical data are provided below:

N-Desmethyl-N-sec-butyl-9-desoxoerythromycin A (Compound I-c). m/z: 762.6 (MH); $^{13}$C-NMR (CDCl$_3$): 178.52, 101.66 and 101.49 (2 sets), 95.18, 81.25, 78.60, 77.84 (2×), 75.11, 74.98, 72.70, 70.73 and 70.40 (2 sets), 69.26 and 69.15 (2 sets), 68.71, 66.46 and 66.38 (2 sets), 64.46, 61.93 and 60.96 (2 sets), 57.67, 49.20, 45.01, 44.62, 43.24, 41.08, 34.70, 33.88 and 33.46 (2 sets), 32.65, 29.16, 28.20 and 28.08 (2 sets), 27.78, 26.80, 25.61, 22.62 and 22.58 (2 sets), 21.64, 21.22 and 21.17 (2 sets), 18.12, 17.25 and 16.68 (2 sets), 16.05, 15.27, 13.96 and 11.59 (2 sets), 11.12 and 11.08 (2 sets), 8.85. I-c is a mixture of two equal amount diastereomers.

N-Desmethyl-N-isobutyl-9-desoxoerythromycin A (Compound I-d). m/z: 762.7 (MH); $^{13}$C-NMR (CDCl$_3$): 178.56, 101.59, 95.11, 81.24, 78.50, 77.90, 77.80, 75.22, 75.00, 72.73, 70.70, 69.40, 68.57, 66.50, 65.67, 61.88, 49.22, 45.00, 44.68, 43.32, 41.20, 37.02, 34.70, 29.53, 29.20, 26.85, 26.10, 25.64, 22.62, 21.69, 21.24, 21.20, 20.61, 20.44, 18.11, 16.06, 15.27, 13.91, 11.17, 8.87.

N-Desmethyl-N-(2-hydroxyethyl)-9-desoxoerythromycin A (Compound I-e). m/z: 750.5 (MH); $^{13}$C-NMR (CDCl$_3$): 178.25, 102.33, 95.33, 82.78, 78.81, 77.99, 77.42, 75.01, 74.91, 72.80, 71.54, 69.30, 68.33, 67.08, 63.59, 58.95, 55.07, 49.19, 44.87, 44.67, 42.80, 41.49, 36.77, 34.68, 31.42, 29.19, 26.75, 25.44, 22.52, 21.66, 21.19, 21.01, 18.00, 16.05, 15.18, 14.00, 11.14, 8.95.

Those skilled in the art will appreciate that the above procedures employing erythromycin A are illustrative and that analogous synthetic sequences can be performed with different starting materials to prepare other compounds of this invention. Compounds in which $R^2$ is Me or F can be prepared from 15-methylerythromycin A or 15-fluoroerythromycin A, respectively. 15-Methylerythromycin A can be prepared as taught in Chu et al., US 2002/0156028 A1 (2002); Ashley et al., US 2002/0094962 A1 (2002); Chu et al., U.S. Pat. No. 6,514,944 B2 (2002) and Chu et al., U.S. Pat. No. 6,762,168 B2 (2004). 15-Fluoroerythromycin A can be prepared as taught in Chu et al., US 2002/0156028 A1 (2002); Ashley et al., U.S. Pat. No. 6,492,562 B1 (2002); Chu et al., U.S. Pat. No. 6,762,168 B2 (2004); and Desai et al., Biotechnol. Prog. 20, 1660–1665 (2000), "Improved Bioconversion of 15-Fluoro-6-deoxyerythronolide B to 15-Fluoroerythromycin A by Overexpression of the eryK Gene in Saccharopolyspora erythraea". The aforementioned documents are incorporated herein by reference. Similarly, by starting with clarithromycin (6-O-Me erythromycin A), erythromycin B or D, or erythromycin C or D, one can make compounds of this invention where $R^3$ is Me, $R^4$ is H, or $R^5$ is H, respectively.

EXAMPLE 3

Motilin Agonist Potency (Cell Based Assay)

The motilin agonist potency of compound I-b was evaluated in a cell based assay, according to the procedure disclosed in Carreras et al., Anal. Biochemistry, 300, 146–151 (2002), the disclosure of which is incorporated herein by reference. Briefly, in this method HEK293 cells are transformed with a synthetic gene for the human motilin receptor. Expression of the synthetic gene produces the human motilin receptor; then the activation of the receptor by the binding of a test compound thereto is measured.

Comparative data is included for two other known motilin agonists, erythromycin A and ABT 229, the latter being a semi-synthetic motilide that entered into—but has since been withdrawn from—clinical trials (Faghih et al., *J. Med. Chem.*, 41, 3402–3408 (1998); Faghih et al., *Drugs of the Future*, 23 (8), 861–872 (1998)).

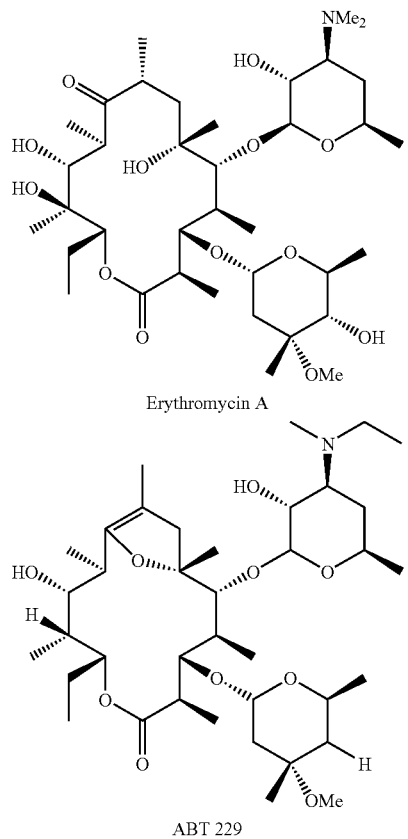

Erythromycin A

ABT 229

The results are provided in Table 1.

TABLE 1

Motilin Agonist Activity

| Compound | Motilin Agonist EC$_{50}$ (µM) |
| --- | --- |
| I-b | 1.2 |
| Erythromycin A (comparative) | 2.0 |
| ABT 229 (comparative) | 0.04[a] |

[a] As reported in Anal. Biochemistry, supra.

EXAMPLE 4

Motilin Agonist Potency (Tissue Based Assay)

The motilin agonist potency of compound I-b also was evaluated using a tissue based assay, using rabbit duodenum tissue-based contractility assay, generally following the procedure of Depoortere et al., *J. Gastrointestinal Motility*, 1, 150–159 (1989), the disclosure of which is incorporated herein by reference. Briefly, this method measures the ability of a compound to induce contractions in rabbit duodenal tissue, a tissue that responds to motilin.

Strips of rabbit duodenum were tested and qualified for use in the assay by as follows. Segments of rabbit duodenum, 20–30 cm distal to the pylorus were split longitudinally. The mucosa was removed and 2×2×15 mm strips of longitudinal smooth muscle were sliced from the segments. The strips were bathed in oxygenated Krebs solution at 37° C., with 1.5 g of tension, and contractions measured auxotonically. Strips exhibiting strong, regular phasic activity (magnitude 0.3 g, FFT peak at 0.3–0.4 Hz, >3-fold stronger than other peaks), and prompt, reproducible responses to 1 uM carbachol ("CCH") (peak contraction in <30 s, >3× phasic magnitude) were qualified for use in the assay; strips not meeting the foregoing criteria were discarded. Qualified strips were mounted on the test apparatus.

Compound I-b was dissolved in dimethylsulfoxide (DMSO) to a final concentration of 10 mM. A series of seven 10× serial dilutions in water was prepared, so that the concentration of the seventh serial dilution was $1.0 \times 10^{-6}$ mM.

The mounted rabbit duodenum strips were dosed with 1 µM carbachol. The carbachol was then washed away by changing the organ bath buffer twice. The strips were washed again 20±5 minutes following the carbachol contraction. Following this last wash a dose response study was initiated within 10±5 min. The first through fifth serial dilutions of the compound were applied, starting with 200 µL of the most dilute solution. After each application, there was a wait of 2±0.5 min, until the response was stable, before the application of the next dose (the next higher concentration serial dilution). The dose was increased in 10-fold increments until a small response was observed. Subsequent doses were the increased in 2- to 5-fold increments, until the maximum response was obtained. At 2±0.5 min after the last drug addition, the strips were dosed with 1 µM carbachol.

The EC$_{50}$ (concentration producing a half-maximal effect) was calculated as follows. The basal tension was subtracted from the compound-induced tension for each reading. The data points were normalized against the response obtained from 1 µM carbachol at the end of the experiment. The concentration of compound was plotted against the response and fitted to the following equation:

$$R = (R_{max} \cdot C)/(EC_{50} + C)$$

where R is the contraction response, R$_{max}$ is the maximal contraction response, and C is the concentration of compound. Both R and R$_{max}$ are expressed as a fraction of the 1 µM carbachol contraction and range from 0 to 1.

The EC$_{90}$ (concentration producing 90% of the maximal effect) was initially approximated as ten times EC$_{50}$. The accuracy of this approximation was then verified by a dose response curve. Qualified duodenum strips were dosed at 0.25·EC$_{90}$. After a maximal response was obtained (2±0.5 min), the dose was increased four-fold. After 2±0.5 min, the strips were dosed with 1 µM carbachol. The difference between the two doses should be in the range of 10–20%. A second set of qualified duodenum strips was dosed at EC$_{90}$. After a maximal response was obtained (2±0.5 min), the dose was increased two-fold. After 2±0.5 min, the strips were dosed with 1 µM carbachol. There should be less than 10% difference between the two doses. In our experience, the accuracy of the initial approximation of EC$_{90}$ was confirmed each time.

EC$_{50}$ and EC$_{90}$ for compound I-b were determined to be 180 nM and 1.8 µM, respectively.

EXAMPLE 5

Antibacterial Activity

The minimum inhibitory concentrations (MICs) for compound I-b against erythromycin A sensitive strains of *S. pneumoniae* were determined using serial dilutions on 96-well microtiter plates. The results are provided in Table 2. The data show that compound I-b has low antibacterial activity, a desirable trait for a prokinetic agent.

TABLE 2

Antibacterial Activity

| S. pneumoniae strain | Minimum Inhibitory Concentration (MIC, μg/mL) | |
| --- | --- | --- |
| | Erythromycin A (comparative) | Compound I-b |
| ATCC 6301 | 0.025 | 50 |
| ATCC 700671 | 0.049 | >200 |
| ATCC 49619 | 0.049 | 50 |

EXAMPLE 6

Cytochrome P450 Inhibition

The inhibitory effect of compound I-b on cytochrome P450 3A4, the most abundant of the cytrochrome P450 enzymes responsible for the metabolism of many drugs, was determined, using a method based on Stresser et al., *Drug Metabolism Disposition*, 30 (7), 845–52. A strong inhibitory effect is undesirable, as indicative of a high probability of interference with other drugs. The $K_i$ for compound I-b was found to be 9.9 μM, comparable to that of erythromycin A.

EXAMPLE 7

Chronic Dosing Tachyphylaxis Model

This example compares the tachyphylaxis (decrement in response after an initial administration; in effect a desensitization to the agonist effect of the compound) of compound I-b, compared to erythromycin A and ABT 229.

Rabbit duodenum strips were qualified as described above and dosed with test compound at its $EC_{90}$ concentration. The contraction was recorded. When peak contractile force was reached, carbachol (1 μM) was added, and any further contraction was recorded. The resulting contraction is expressed as a fraction of the 1 μM carbachol contraction. The test compound and carbachol were washed away by changing the bath solution twice. The procedure was repeated at 30, 60, and 90 min following the initial dosing.

The contractile responses at 0, 30, 60, and 90 min were plotted as shown in FIG. 1, with the response at time 0 min arbitrarily set as 100% for each tested compound. The data in FIG. 1 shows that the tachyphylaxis effect for compound I-b is distinctly less pronounced than that of ABT 229.

Using this procedure, compound I-b was found to induce 39±13% of the initial contraction after the fourth dose and compound I-e was found to induce 85±11% of the initial contraction after the fourth dose.

EXAMPLE 8

Tachphylaxis Recovery Model

In this study, the tachyphylaxis was measured in terms of the time needed, after an initial dose, for response to a test compound to recover to the original levels. The compounds tested were compound I-b, erythromycin A, motilin, and ABT 229.

Figure 2:
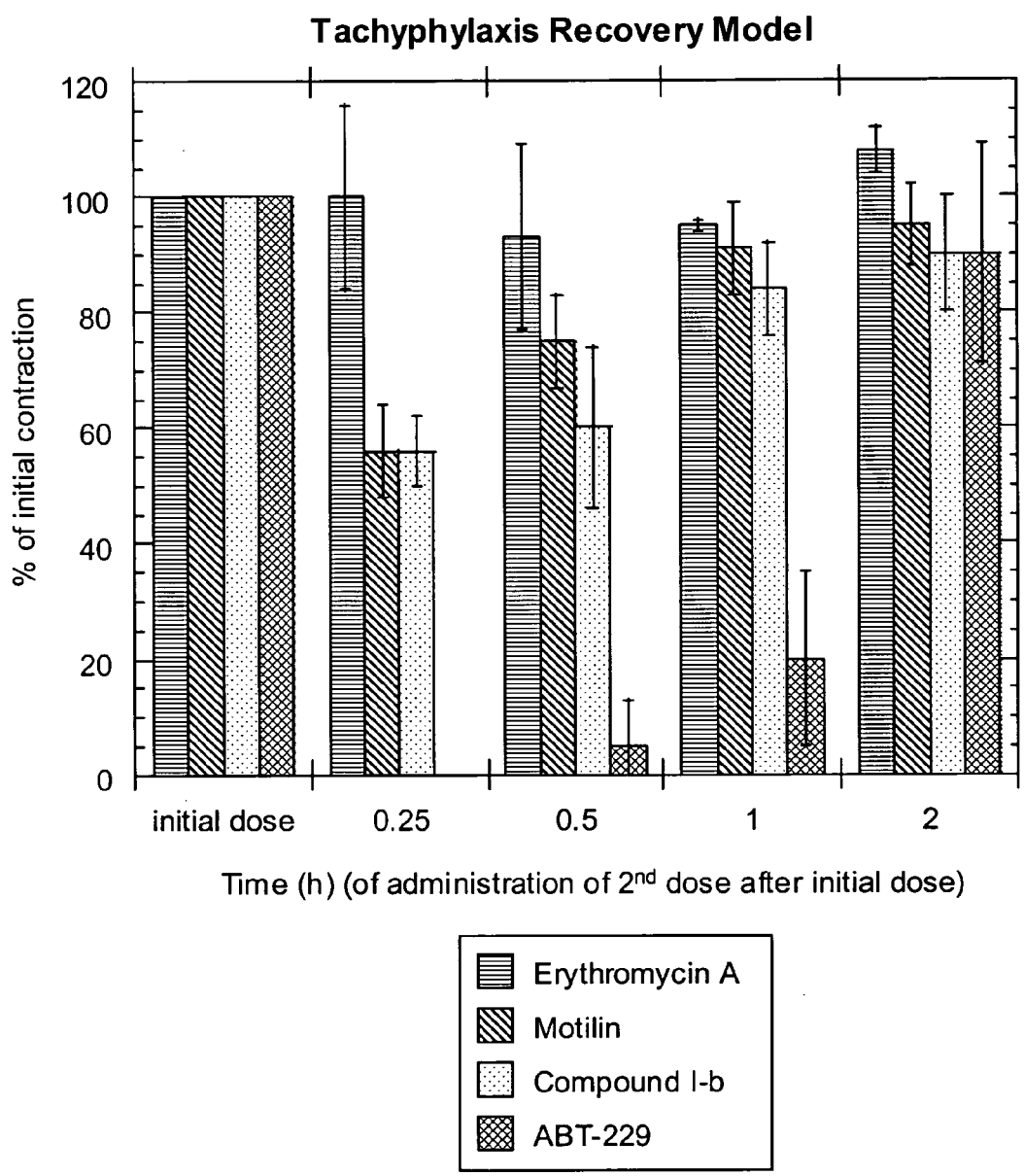
FIG. 2 shows the results for a tachyphylaxis recovery model for a compound of this invention.

Rabbit duodenum muscle strips qualified per the preceding examples were dosed with the test compound at its $EC_{90}$ concentration, as described in the preceding example. After the initial dosing, the test compound and carbachol were removed by changing the bath solution twice. After waiting for a variable amount of time (0.25, 0.5, 1, or 2 hr) a second dose was administered. The responses (normalized for against the carbachol response and arbitrarily set as 100% for the initial dose) are plotted in FIG. 2. The data show that compound I-b has a recovery time comparable to that of motilin itself and noticeably shorter than that of ABT 229.

In a preferred embodiment, compounds of this invention possess at least one of the following attributes: (a) an MIC of 50 μg/mL or greater against each of *S. pneumoniae* ATCC 6301, 700671, and 49619; (b) an $EC_{50}$ of 2.0 μM or lesser as a motilin agonist when measured by the cell-based assay of Example 3, and (c) a recovery of 60% or more of the initial dosing efficacy after 1 hr, as measured by the tachyphylaxis recovery model of Example 8. More preferably, compounds of this invention possess at least two of attributes (a), (b) and (c). Even more preferably, compounds of this invention possess all three of attributes (a), (b) and (c).

EXAMPLE 8 hERG Channel Inhibition

The pro-arrhythmic effects of erythromycin and related compounds have been attributed to their inhibition of the hERG (human ether-a-go-go related gene) potassium channel. Stanat et al., *Mol. Cellular Biochem.*, 254, 1–7 (2003), "Characterization of the Inhibitory Effects of Erythromycin and Clarithromycin on the HERG Potassium Channel". The hERG channel inhibitory effects of compounds of this invention were evaluated using the technique reported in the Stanat et al. paper, with results presented in Table 4, including comparative data against erythromycin A and ABT-229. The results show that compounds of this invention have lower hERG potassium channel inhibition values than reference motilide compound ABT-229, though those values are still higher than for erythromycin A.

TABLE 3 hERG Potassium Channel Inhibition

| Compound | Inhibition (%) at Specified Compound Concentration | |
| --- | --- | --- |
| | 10 μM | 30 μM |
| I-b | 74 | 95 |
| I-c | 26.5 | 70.3 |
| I-d | 33.1 | 71.4 |
| I-e | 57.1 | 84.3 |
| Erythromycin A | 11.5 | 29 |
| ABT-229 | 96 | 98 |

The foregoing detailed description of the invention includes passages that are chiefly or exclusively concerned with particular parts or aspects of the invention. It is to be understood that this is for clarity and convenience, that a particular feature may be relevant in more than just the passage in which it is disclosed, and that the disclosure herein includes all the appropriate combinations of information found in the different passages. Similarly, although the various figures and descriptions herein relate to specific embodiments of the invention, it is to be understood that where a specific feature is disclosed in the context of a particular figure or embodiment, such feature can also be used, to the extent appropriate, in the context of another figure or embodiment, in combination with another feature, or in the invention in general.

Further, while the present invention has been particularly described in terms of certain preferred embodiments, the invention is not limited to such preferred embodiments. Rather, the scope of the invention is defined by the appended claims.

We claim:

1. A compound having a structure according to formula I:

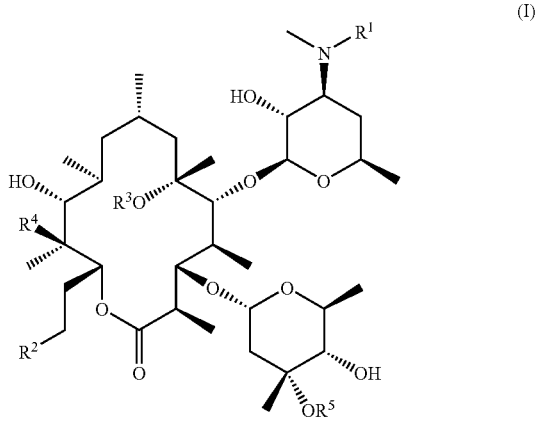

(I)

and the pharmaceutically acceptable salts, solvates, hydrates, and esters thereof, wherein $R^1$ is $C_2$–$C_5$ alkyl, $C_2$–$C_5$ alkenyl, or $C_2$–$C_5$ alkynyl;
$R^2$ is H, Me, or F;
$R^3$ is H or Me;
$R^4$ is H or OH; and
$R^5$ is H or Me.

2. A compound according to claim 1, having a structure according to formula Ia

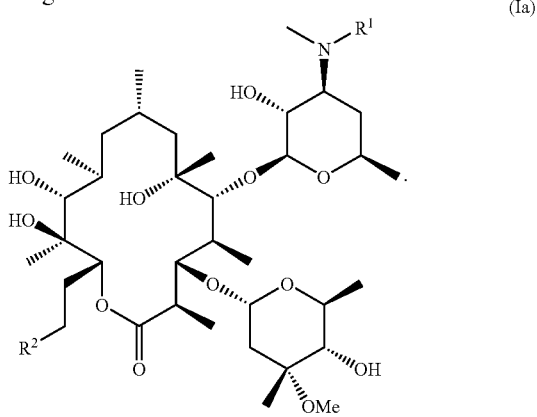

(Ia)

3. A compound according to claim 2, wherein $R^2$ is H.

4. A compound according to claim 3, wherein $R^1$ is isopropyl, sec-butyl, n-propyl, 2-hydroxyethyl, 2-hydroxy-2-methylpropyl, t-butyl, 2-ethoxyethyl, or isobutyl.

5. A compound according to claim 3, wherein $R^1$ is isopropyl, sec-butyl, 2-hydroxyethyl, or isobutyl.

6. A compound according to claim 3, wherein $R^1$ is isopropyl.

7. A compound according to claim 3, wherein $R^1$ is 2-hydroxyethyl.

8. A method for treating a disorder of gastric motility in a subject suffering from such disorder, comprising administering to a subject in need of such treatment a therapeutically effective dose of a compound according to claim 1.

9. A method according to claim 8, wherein the disorder of gastric motility is gastroparesis, gastroesophageal reflux disease, anorexia, gall bladder stasis, postoperative paralytic ileus, scleroderma, intestinal pseudoobstruction, gastritis, emesis, or chronic constipation (colonic inertia).

10. A method according to claim 8, wherein the compound having a structure according to claim 1 has a structure according to formula Ia:

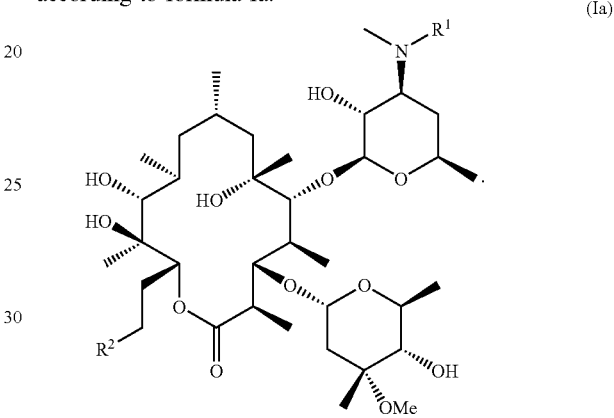

(Ia)

11. A method according to claim 10, wherein $R^1$ is isopropyl, sec-butyl, n-propyl, 2-hydroxyethyl, 2-hydroxy-2-methylpropyl, t-butyl, 2-ethoxyethyl, or isobutyl and $R^2$ is H.

12. A method according to claim 10, wherein $R^1$ is isopropyl and $R^2$ is H.

13. A method according to claim 10, wherein $R^1$ is 2-hydroxyethyl and $R^2$ is H.

14. A method for stimulating the action of the motilin receptor, comprising contacting the motilin receptor with a compound having a structure according to claim 1.

15. A method according to claim 14, wherein the compound having a structure according to claim 1 has a structure according to formula Ia:

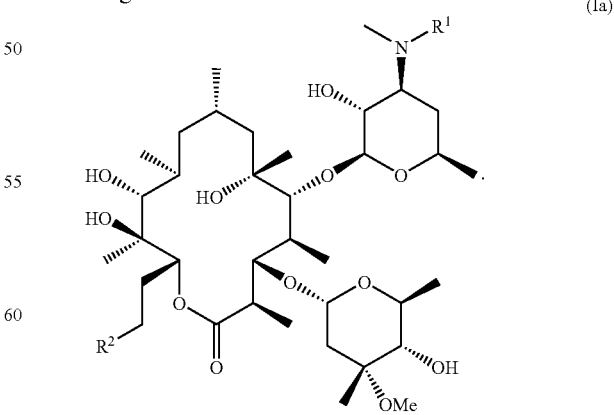

(Ia)

* * * * *